United States Patent
Samuelson et al.

(10) Patent No.: US 6,794,172 B2
(45) Date of Patent: Sep. 21, 2004

(54) **METHOD FOR CLONING AND EXPRESSION OF PPUMI RESTRICTION ENDONUCLEASE AND PPUMI METHYLASE IN *E. COLI***

(75) Inventors: James Samuelson, Danvers, MA (US); Shuang-yong Xu, Lexington, MA (US)

(73) Assignee: New England Biolabs, Inc., Beverly, MA (US)

( * ) Notice: Subject to any disclaimer, the term of this patent is extended or adjusted under 35 U.S.C. 154(b) by 328 days.

(21) Appl. No.: 10/150,048

(22) Filed: May 17, 2002

(65) Prior Publication Data

US 2003/0215907 A1 Nov. 20, 2003

(51) Int. Cl.[7] .............................. C12N 9/22; C12N 15/55
(52) U.S. Cl. ................ 435/199; 435/320.1; 435/252.3; 536/23.2
(58) Field of Search .............................. 435/199, 320.1, 435/252.3; 536/23.2

(56) References Cited

U.S. PATENT DOCUMENTS

| | | |
|---|---|---|
| 5,200,333 A | 4/1993 | Wilson |
| 5,498,535 A | 3/1996 | Fomenkov et al. |

OTHER PUBLICATIONS

Bougueleret, et al., Nucl. Acids Res. 12:3659–3676 (1984).
Fomenkov, et al., Nucl. Acids Res. 22:2399–2403 (1994).
Gingeras and Brooks, Proc. Natl. Acad. Sci. 80:402–406 (1983).
Kiss, et al., Nucl. Acids Res. 13:6403–6421 (1985).
Kiss and Baldauf, Gene 21:111–119 (1983).
Kosykh, et al., Mol. Gen. Genet. 178:717–718 (1980).
Malone, et al., J. Mol. Biol. 253:618–632 (1995).
Mann, et al., Gene 3:97–112 (1978).
New England Biolabs' catalog 2000–2001, p. 220.
Roberts, et al., Nucl. Acids Res. 29:268–269 (2001).
Szomolanyi, et al., Gene 10:219–225 (1980).
Walder, et al., J. Biol. Chem. 258:1235–1241 (1983).
Walder, et al., Proc. Natl. Acad. Sci. USA 78:1503–1507 (1981).
Wayne, et al., Gene 202–83–88 (1997).
Kong, et al., Nucleic Acids Res. 28:3216–3223 (2000).

*Primary Examiner*—Charles L. Patterson, Jr.
(74) *Attorney, Agent, or Firm*—Gregory D. Williams; Harriet M. Strimpel

(57) ABSTRACT

The present invention relates to recombinant DNA encoding the PpuMI restriction endonuclease as well as PpuMI methylase, expression of PpuMI restriction endonuclease and PpuMI methylase in *E. coli* cells containing the recombinant DNA.

6 Claims, 7 Drawing Sheets

Figure 2-1

```
     ATGAGTCAGAAAAAGCTAAAAGTGATATCTCTGTTTTCAGGGGGGATGGGCCTAGACCTT
  1  ------------+---------+---------+---------+---------+---------+  60
      M  S  Q  K  K  L  K  V  I  S  L  F  S  G  G  M  G  L  D  L
     GGCCTCAAAGAGACTGAAAGATACGAACTTCTAGCATGTGTTGAGAAAGTTCCAGCTTAC
 61  ---------+---------+---------+---------+---------+---------+ 120
      G  L  K  E  T  E  R  Y  E  L  L  A  C  V  E  K  V  P  A  Y
     TGCGAAACGATCCGTCTTAATAGAGACGCCGGTCGCCTACCTGCAGGTATGAAACTCTAT
121  ---------+---------+---------+---------+---------+---------+ 180
      C  E  T  I  R  L  N  R  D  A  G  R  L  P  A  G  M  K  L  Y
     GAGGGCGACATCACGAATGTTGACCCTTATGATGTTATGGCCGCAACTGGAATTAAGCCC
181  ---------+---------+---------+---------+---------+---------+ 240
      E  G  D  I  T  N  V  D  P  Y  D  V  M  A  A  T  G  I  K  P
     GGTGAGCTTGACGTATTGGTAGGGGGGCCACCTTGCCAATCATTTAGCACAGCTGGCAAT
241  ---------+---------+---------+---------+---------+---------+ 300
      G  E  L  D  V  L  V  G  G  P  P  C  Q  S  F  S  T  A  G  N
     CGGGGGACCGTACAAGACCCTCGGGGTACTCTGCTGTGGCAATTCCTAAAGTTTGTTGAA
301  ---------+---------+---------+---------+---------+---------+ 360
      R  G  T  V  Q  D  P  R  G  T  L  L  W  Q  F  L  K  F  V  E
     GTCCTTCAGCCAAAGTTCTTCCTGATGGAGAACGTACGTGGATTGATTTCTGCTGCACTG
361  ---------+---------+---------+---------+---------+---------+ 420
      V  L  Q  P  K  F  F  L  M  E  N  V  R  G  L  I  S  A  A  L
     AGGCATCGCCCCATTGCTGAGCGCCCTCCAAAAGGTCCAGAGCTATCAGTTGATGAAATG
421  ---------+---------+---------+---------+---------+---------+ 480
      R  H  R  P  I  A  E  R  P  P  K  G  P  E  L  S  V  D  E  M
     CCTGGATCAGTCATTCGGCTATTCTCTCAAGATCTCCAGAGACTTGAAGCCAAGTACCAT
481  ---------+---------+---------+---------+---------+---------+ 540
      P  G  S  V  I  R  L  F  S  Q  D  L  Q  R  L  E  A  K  Y  H
     CTGGATGTATTCGAGGTAAACTCCGTTAATTACGGAGCTCCTCAAATTCGTGAGCGAGTC
541  ---------+---------+---------+---------+---------+---------+ 600
      L  D  V  F  E  V  N  S  V  N  Y  G  A  P  Q  I  R  E  R  V
     CTTTTCATAGGAAATCGTTTTGGGGCACAGGTCGCGTTCCCAGATCCAACCCACGGCCCT
601  ---------+---------+---------+---------+---------+---------+ 660
      L  F  I  G  N  R  F  G  A  Q  V  A  F  P  D  P  T  H  G  P
     GTAGATGGGTTGGATGCAGAAGATGATCTCTTTGGCACAAGCTCAAAGCTCAAAGGCTGG
661  ---------+---------+---------+---------+---------+---------+ 720
      V  D  G  L  D  A  E  D  D  L  F  G  T  S  S  K  L  K  G  W
     CGCTCCTTGGGTGACGTGATATCTGATCTTCATGAGATCGCACCTGAGATTATGGACTTC
721  ---------+---------+---------+---------+---------+---------+ 780
      R  S  L  G  D  V  I  S  D  L  H  E  I  A  P  E  I  M  D  F
     AGCCCAAGGAAGAAATCTTTCCTTGAGATGGTTCCAGAGGGTTCAAACTGGCGAAGTCTG
781  ---------+---------+---------+---------+---------+---------+ 840
      S  P  R  K  K  S  F  L  E  M  V  P  E  G  S  N  W  R  S  L
     CCAGAAGAAATTCAAAAGGAATCAATGGGAAAGGCCTGGCTGGCGAAGGGGGGCGGTCT
841  ---------+---------+---------+---------+---------+---------+ 900
      P  E  E  I  Q  K  E  S  M  G  K  A  W  L  A  K  G  G  R  S
```

Figure 2-2

```
         GGTTGGTGGAGGAGACTTACCATGGACCTCCCATGCCCCACTCTGGTAACGATGCCAAAT
 901     ---------+---------+---------+---------+---------+---------+ 960
         G  W  W  R  R  L  T  M  D  L  P  C  P  T  L  V  T  M  P  N
         CACTCAAGTACATCACTGTGCCATCCGGTGCATACTCGAGCGCTCTCTGTGAGGGAATAT
 961     ---------+---------+---------+---------+---------+---------+ 1020
         H  S  S  T  S  L  C  H  P  V  H  T  R  A  L  S  V  R  E  Y
         GCGCGAATTCAAGAGTTCCCTGATTACTGGGAGTTCGCAGGAAAAATCGCCGATAAATAT
1021     ---------+---------+---------+---------+---------+---------+ 1080
         A  R  I  Q  E  F  P  D  Y  W  E  F  A  G  K  I  A  D  K  Y
         GCGCAGATAGGAAATGCTGTGCCCGTGAGGTTAGGCAAAGTAGCCGGCGAGGTGATTGCA
1081     ---------+---------+---------+---------+---------+---------+ 1140
         A  Q  I  G  N  A  V  P  V  R  L  G  K  V  A  G  E  V  I  A
         AAGTGCTATGATGAGCTACAGGCGAATGGGTGGCTGCCTCTGGCGCAGGCTCCCGAAGCT
1141     ---------+---------+---------+---------+---------+---------+ 1200
         K  C  Y  D  E  L  Q  A  N  G  W  L  P  L  A  Q  A  P  E  A
         TTCAGGATCGTTTATATACAGTCTCATGTGCGTACTCGACGTTGGTTCAAAGACGGCAAA
1201     ---------+---------+---------+---------+---------+---------+ 1260
         F  R  I  V  Y  I  Q  S  H  V  R  T  R  R  W  F  K  D  G  K
         ACAATTGTCTGGGATAAAGAAACTGACGAAGCGGACTACGGACAGTCAAAAACCAAGCGC
1261     ---------+---------+---------+---------+---------+---------+ 1320
         T  I  V  W  D  K  E  T  D  E  A  D  Y  G  Q  S  K  T  K  R
         CTTGTGAAGGCCTTGGCTTAA
1321     ---------+---------+- 1341
         L  V  K  A  L  *
```

Figure 3-1

```
     ATGGCAAAAGGGCATCCAGGACTACCCAAACCGAACGTCGTTACTTTCTCGAAGAGTGAG
  1  ---------+---------+---------+---------+---------+---------+  60
     M  A  K  G  H  P  G  L  P  K  P  N  V  V  T  F  S  K  S  E
     CTACTCGAGCAACTAATGGCTGTTGATCTCGACCCGAGTGCTAGAGCAAGAGCTCTTGCT
 61  ---------+---------+---------+---------+---------+---------+ 120
     L  L  E  Q  L  M  A  V  D  L  D  P  S  A  R  A  R  A  L  A
     ATGGAAGAGCAATTCCGGAGAAAGATCGATTCGCACGTGGGATCCCTAACCGCTGCCGAT
121  ---------+---------+---------+---------+---------+---------+ 180
     M  E  E  Q  F  R  R  K  I  D  S  H  V  G  S  L  T  A  A  D
     GCCAAATTTAATAAGTTTTTCACCAGTCCGTATGTCTTGCTGATGCATGCTCGAAAAAAT
181  ---------+---------+------   -+---------+---------+---------+ 240
     A  K  F  N  K  F  F  T  S  P  Y  V  L  L  M  H  A  R  K  N
     CGCTACACAAGAGTTAGCGAGATCGAGCATGACATCCTTCCTGCAAAGCTATTTTCGTCC
241  ---------+---------+---------+---------+---------+---------+ 300
     R  Y  T  R  V  S  E  I  E  H  D  I  L  P  A  K  L  F  S  S
     ATGGAAACCTCTGCTGGTAGAGCGGTAGAAATTATCGCACTTCCAGTATACGGATGGACT
301  ---------+---------+---------+---------+---------+---------+ 360
     M  E  T  S  A  G  R  A  V  E  I  I  A  L  P  V  Y  G  W  T
     CCTGTCGTAAGCGCAATGCACTCTGCAAATTCTGCTCTTGACGGGCTGCGCGTGAATGGC
361  ---------+---------+---------+---------+---------+---------+ 420
     P  V  V  S  A  M  H  S  A  N  S  A  L  D  G  L  R  V  N  G
     GATACACTTCAGGTTGCGACTTTAAAGAGTGGTCCGCGCTGCCTGAATGATGAGATGAGC
421  ---------+---------+---------+---------+---------+---------+ 480
     D  T  L  Q  V  A  T  L  K  S  G  P  R  C  L  N  D  E  M  S
     GAGAATTTCGCAGATACCATTATTGCAAATCTCGAGGCCTGGGCTAATCAGCATGATGTG
481  ---------+---------+---------+---------+---------+---------+ 540
     E  N  F  A  D  T  I  I  A  N  L  E  A  W  A  N  Q  H  D  V
     CGGAAAGTGGAGTTTACCTATGGGGTTCTATATGGAACTCAAAAGGTTTCGAATAAGAAA
541  ---------+---------+---------+---------+-------  +---------+ 600
     R  K  V  E  F  T  Y  G  V  L  Y  G  T  Q  K  V  S  N  K  K
     GATTGGCACATATTCAAGAACCTCGCTTTGAAATTACCCGAGGGCAGTTTTTCCGTCCTC
601  ---------+---------+---------+---------+---------+---------+ 660
     D  W  H  I  F  K  N  L  A  L  K  L  P  E  G  S  F  S  V  L
     CCCAATGGACGCTGGGATTGCAGTTTCGCATACAAAGGCATTGAAGTAGAGGCTGGGATT
661  ---------+---------+---------+---------+---------+---------+ 720
     P  N  G  R  W  D  C  S  F  A  Y  K  G  I  E  V  E  A  G  I
     CGGATCGGAAAAGATTGGTGGACTCATCTAGGTGGGAGATTGGGATTGGCGGAGCTAGCA
721  ---------+---------+---------+---------+---------+---------+ 780
     R  I  G  K  D  W  W  T  H  L  G  G  R  L  G  L  A  E  L  A
     ATTGCCCTAATCCGTGCTTGCATCGCGCCCGGTGATTTGGATGCGGAGGATCATGGATAC
781  ---------+---------+---------+---------+---------+---------+ 840
     I  A  L  I  R  A  C  I  A  P  G  D  L  D  A  E  D  H  G  Y
     ACCATCAAGGATTTGCACAGTATTGTTTCCTTGCAAGCCGTCCCGGATGGTTTCAATCCC
841  ---------+---------+---------+---------  +--------+---------+ 900
     T  I  K  D  L  H  S  I  V  S  L  Q  A  V  P  D  G  F  N  P
```

Figure 3-2

```
         GCGATCCTTCAGCGTAGTCAGATAGCATGGTTCTTCTTCTTTATGAGGCACTTCTGCGAC
   901   ---------+---------+---------+---------+---------+---------+ 960
          A  I  L  Q  R  S  Q  I  A  W  F  F  F  F  M  R  H  F  C  D
         TCTATGGTCGAAGGCTTTCCGTATGTTGACACCTGCTCAAGTGCTGTCCCAGTCAGCGCA
   961   ---------+---------+---------+---------+---------+---------+ 1020
          S  M  V  E  G  F  P  Y  V  D  T  C  S  S  A  V  P  V  S  A
         CATATCCATGAAGTCGCTCAGGCGTGGTGA
  1021   ---------+---------+---------+ 1050
          H  I  H  E  V  A  Q  A  W  *
```

METHOD FOR CLONING AND EXPRESSION OF PPUMI RESTRICTION ENDONUCLEASE AND PPUMI METHYLASE IN *E. COLI*

BACKGROUND OF THE INVENTION

The present invention relates to recombinant DNA that encodes the PpuMI restriction endonuclease (PpuMI endonuclease or PpuMI) as well as PpuMI methyltransferase (PpuMI methylase or M.PpuMI), and expression of PpuMI endonuclease and methylase in *E. coli* cells containing the recombinant DNA.

PpuMI endonuclease is found in the bacterium *Pseudomonas putida* (NEB#372, New England Biolabs, Beverly, Mass.). It recognizes the double-stranded DNA sequence 5'RG/GWCCY3' (W=A or T, R=A or G, Y=C or T, / indicates the cleavage position) and cleaves between the two guanines to generate 3-base cohesive ends. Due to degeneracy at the central position of the recognition sequence, the cohesive ends derived from two different PpuMI sites may or may not be complementary. PpuMI methylase (M.PpuMI) is also found in the same strain and it recognizes the same DNA sequence as PpuMI endonuclease. M.PpuMI displays homology to the C5-cytosine DNA methyltransferase family. Therefore, M.PpuMI presumably methylates the C5 position of one of the cytosines present within the recognition sequence to protect DNA from PpuMI endonuclease cleavage. The substrate for M.PpuMI may be non-methylated or hemi-methylated DNA.

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') along DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and twenty-eight restriction endonucleases with unique specificities have been identified among the many hundreds of bacterial species that have been examined to date (Roberts and Macelis, *Nucl. Acids Res.* 29:268–269 (2001)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5'TTT/AAA3', 5'RG/GNCCR3' and 5'CACNNN/GTG3' respectively. *Escherichia coli* RY13, on the other hand, produces only one enzyme, EcoRI, which recognizes the sequence 5'G/AATTC3'.

It is thought that in nature, restriction endonucleases play a protective role in the welfare of the bacterial cells. The enzymes cleave invading foreign DNA molecules such as plasmids or viral DNA that would otherwise destroy or parasitize the bacteria while the host bacterial DNA remains intact. The cleavage that takes place disables many of the infecting genes and renders the DNA susceptible to further degradation by non-specific nucleases.

A second component of the bacterial protective systems are the modification methylases that protect host DNA from cleavage with restriction endonuclease with which they coexist. The restriction endonuclease and modification methylase form the restriction-modification (R-M) system. The methylase provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group to produce C5 methyl cytosine, N4 methyl cytosine, or N6 methyl adenine. Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiable foreign DNA, is susceptible to restriction endonuclease recognition and cleavage. During and after DNA replication, usually hemi-methylated DNA (DNA methylated on one strand) is also resistant to the cognate restriction endonuclease.

With the advancement of recombinant DNA technology, it is now possible to clone restriction-modification genes and overproduce the enzymes in large quantities. The key to isolating clones of restriction-modification genes is to develop an efficient method to identify such clones within genomic DNA libraries, (i.e. populations of clones derived by 'shotgun' procedures) when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., *Mol. Gen. Genet.* 178:717–719 (1980); HhaII: Mann et al., *Gene* 3:97–112 (1978); PstI: Walder et al., *Proc. Nat. Acad. Sci.* 78:1503–1507 (1981)). Since the expression of restriction-modification systems in bacteria enables them to resist infection by bacteriophages, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into *E. coli* cloning vectors (EcoRV: Bougueleret et al., *Nucl. Acids. Res.* 12:3659–3676 (1984); PaeR7: Gingeras and Brooks, *Proc. Natl. Acad. Sci. USA* 80:402–406 (1983); Theriault and Roy, *Gene* 19:355–359 (1982); PvuII: Blumenthal et al., *J. Bacteriol.* 164:501–509 (1985); Tsp45I: Wayne et al. *Gene* 202:83–88 (1997)).

A third approach is to select for active expression of methylase genes (methylase selection) (U.S. Pat. No. 5,200, 333 and BsuRI: Kiss et al., *Nucl. Acids. Res.* 13:6403–6421 (1985)). Since restriction-modification genes are often closely linked together, both genes can often be cloned simultaneously. This selection does not always yield a complete restriction system however, but instead yields only the methylase gene (BspRI: Szomolanyi et al., *Gene* 10:219–225 (1980); BcnI: Janulaitis et al., *Gene* 20:197–204 (1982); BsuRI: Kiss and Baldauf, *Gene* 21:111–119 (1983); and PstI: Walder et al., *J. Biol. Chem.* 258:1235–1241 (1983)).

A more recent method, the "endo-blue method", has been described for direct cloning of thermostable restriction endonuclease genes into E. coli based on the indicator strain of E. coli containing the dinD::lacZ fusion (Fomenkov et al., U.S. Pat. No. 5,498,535, (1996); Fomenkov et al., Nucl. Acids Res. 22:2399–2403 (1994)). This method utilizes the E. coli SOS response signal following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535). The disadvantage of this method is that some positive blue clones containing a restriction endonuclease gene are difficult to culture due to the lack of the cognate methylase gene.

There are three major groups of methyltransferases identified as C5-cytosine methylases, and the amino-transferases—N4-cytosine methylases and N6-adenine methylases. (Malone et al. J. Mol. Biol. 253:618–632 (1995)). These groups of methylases derive their names from the position and the base that is modified. When a restriction site on DNA is modified (methylated) by the methylase, it is resistant to digestion by the cognate restriction endonuclease. Sometimes methylation by a non-cognate methylase can also confer DNA sites resistant to restriction digestion. For example, Dcm methylase modification of 5'CCWGG3' (W=A or T) can also make the DNA resistant to PspGI restriction digestion. Another example is that CpG methylase can modify the CG dinucleotide of the NotI site (5'GCGGCCGC3') and make it refractory to NotI digestion (New England Biolabs' Catalog, page 220 (2000–2001)). Therefore methylases can be used as a tool to modify certain DNA sequences and make them uncleavable by restriction enzymes.

Type II methylase genes have been found in many sequenced bacterial genomes (GenBank, http://www.ncbi.nlm.nih.gov; and Rebase™, http://rebase.neb.com/rebase). Direct cloning and over-expression of ORFs adjacent to methylase genes yielded restriction enzymes with novel specificities (Kong et al. Nucl. Acids Res. 28:3216–3223 (2000)). Thus microbial genome mining emerged as a new way of screening/cloning new type II restriction enzymes and methylases and their isoschizomers.

Because purified restriction endonucleases and modification methylases are useful tools for creating recombinant DNA molecules in the laboratory, there is a strong commercial interest to obtain bacterial strains through recombinant DNA techniques that produce large quantities of restriction enzymes and methylases. Such over-expression strains should also simplify the task of enzyme purification.

SUMMARY OF THE INVENTION

The present invention relates to a method for cloning the PpuMI restriction endonuclease gene (ppuMIR) and the PpuMI methylase gene (ppuMIM) from Pseudomonas putida into E. coli. The ppuMIR gene was cloned by inverse PCR and direct PCR from genomic DNA using oligonucleotide primers that were based on the DNA sequences obtained via methylase selection.

The initial difficulty was to select the functional PpuMI methylase gene from a plasmid library. The first plasmid library was generated by ligation of PpuMI genomic DNA fragments into pBR322 and transformation into E. coli. Plasmid pBR322 contains two PpuMI sites downstream of the tetracycline resistance gene (Tet). However, one site is blocked by dcm methylation so, effectively, only one site is useful for the methylase selection procedure. Primary library DNA was incubated with PpuMI endonuclease to select for undigested plasmids containing methylated PpuMI sites. When the challenged DNA was transformed into E. coli a small number of colonies contained pBR322 clones. However, none of the plasmid isolates from these colonies contained the ppuMIM gene. Failure to select the ppuMIM gene could have been due to many factors. The most probable reason for failure of the methylase selection procedure is inadequate expression of the methylase gene in E. coli. To address this potential problem, plasmid libraries were created in a high-copy derivative of pUC18, designated pJS105-22. Plasmid pJS105-22 contains the chloramphenicol resistance gene (Cam) in place of the ampicillin resistance gene (Amp). But most importantly, pJS105-22 contains three PpuMI sites to reduce the number of false positives attributed to incomplete digestion during the challenge step of the methylase selection. By transforming E. coli with a library of pJS105-22 plasmids, the ppuMIM gene was isolated in twenty-two of thirty-six clones resulting from the methylase selection procedure. The insert DNA of clone 2A was confirmed to contain a gene homologous to the C5-cytosine methyltransferase family. This gene was presumed to be the ppuMIM gene since it displayed homology to the Eco109I methylase, which modifies the nearly identical sequence RG/GNCCY.

The ppuMIR gene was identified by sequencing the genes adjacent to the ppuMIM gene. Inverse PCR walking identified an open reading frame downstream of ppuMIM. This 975 bp ORF starting with the first ATG (92 bp downstream from the ppuMIM stop codon) was PCR-amplified from genomic DNA and cloned into expression vector pJS12T, which was created by modification of pR976 (NEB collection, New England Biolabs; Beverly, Mass.). However, PpuMI restriction activity was not detected in the E. coli cell extract of fourteen recombinant clones. In addition, this downstream ORF did not display homology to the eco109I restriction endonuclease gene as might be expected. Consequently, the region upstream of the ppuMIM gene was sequenced to possibly identify an ORF encoding the ppuMIR gene. Located approximately 650 bp upstream of ppuMIM a significant ORF was discovered but the hypothetical protein sequence displayed similarity to transposase proteins of various bacteria. Therefore, the downstream ORF was re-evaluated. Upon re-evaluation, an in-frame GTG codon was found only 17 bp downstream from the ppuMIM stop codon. The GTG sequence codes for valine and in some cases can be used for initiation of translation. The downstream region was again PCR-amplified from genomic DNA to give an ORF of 1050 bp. In this case, the 5' forward primer contained an NdeI site that created a GTG to ATG mutation and allowed cloning into the NdeI site of expression vector pJS12T. Of fourteen clones analyzed for activity, ten displayed restriction activity identical to native PpuMI endonuclease. The recombinant PpuMI R-M system [pJS12T-PpuMIR, pSYX20-PpuMIM] within E. coli host ER2502 provides $2.4 \times 10^5$ units per gram of wet cells.

BRIEF DESCRIPTION OF THE DRAWINGS

FIG. 2. PpuMI methylase gene sequence (SEQ ID NO: 1) (ppuMIM, 1341 bp) and the encoded amino acid sequence (SEQ ID NO: 2).

FIG. 3. PpuMI endonuclease gene sequence (SEQ ID NO: 3) (ppuMIR, 1050 bp) and the encoded amino acid sequence (SEQ ID NO: 4).

DETAILED DESCRIPTION OF THE INVENTION

Figure 1:
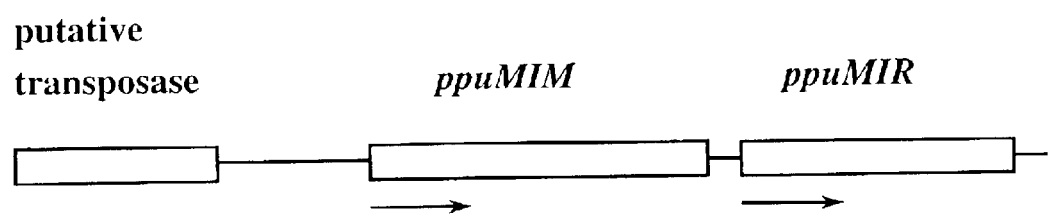
FIG. 1. Gene organization of PpuMI R-M system, ppuMIR, PpuMI restriction endonuclease gene; ppuMIM, PpuMI methylase gene.

The first step to cloning the recombinant PpuMI R-M system in *E. coli* was to isolate the functional methylase gene in order to pre-protect the host genomic DNA against expression of the cognate endonuclease gene. A specific vector was designed for selection of the ppuMIM from a plasmid library. Library vector pJS105-22 was created from pUC18 and contains the following features to enable selection of ppuMIM.

(a) The RNAII primer promoter essential for plasmid replication was replaced with a promoter containing a PpuMI site between the −35 and −10 region. In addition, the *E. coli* yidC gene was inserted into the HindIII and SfoI sites of the polylinker to provide two additional PpuMI sites. A total of three PpuMI sites within pJS105-22 serves to significantly decrease the number of false positives, which may occur during the methylase selection procedure. Most importantly, cleavage of the PpuMI site within the RNAII primer promoter should not allow the plasmid to regain replication competence once a linearized DNA fragment is taken up by the cell during transformation of the challenged library.

(b) The modified origin of replication containing a PpuMI site provides a high copy number equal to or greater than pUC18. This characteristic is important as a high ppuMIM copy number increases the concentration of the gene product in the cell and increases the potential for complete methylation protection of library plasmids carrying ppuMIM.

After selection of the functional ppuMIM gene, subcloning of the ppuMIM gene and pre-protection of an *E. coli* host, the final step was cloning of the PpuMI endonuclease gene. Inverse PCR walking was conducted to identify the ppuMIR gene within the DNA sequence flanking ppuMIM. The putative ppuMIR gene was amplified by PCR from genomic DNA. Following purification and ethanol precipitation, the PCR DNA was digested with NdeI and EcoRI and ligated to pJS12T with compatible ends. The ligated DNA was transformed into pre-modified host ER2502 [pSYX20-PpuMIM] to obtain Tet$^R$ Kan$^R$ transformants. Cell extract was prepared from fourteen transformants after growing 10 ml cultures to mid-log phase and inducing with 0.5 mM IPTG for 3 hours. Ten of fourteen clones were found to exhibit PpuMI endonuclease activity. Vector pJS105-22 was used as the substrate for activity determination. Complete digestion by 4 units native PpuMI results in the production of three fragments of approximately 2.0, 1.6 and 1.2 kb (see lane 2 of FIG. 4). Cell extract from clones PP2 and PP3 provided complete digestion at a 1:10 dilution and partial activity at a 1:100 dilution (FIG. 4) indicating overexpression of PpuMI endonuclease from the tac promoter of pJS12T.

The final recombinant PpuMI R-M system is composed of ppuMIM constitutively expressed from the Tet promoter of pSYX20 and ppuMIR expressed from the low-copy, IPTG-inducible vector pJS12T. The method described herein by which the ppuMIM and ppuMIR genes are preferably cloned and expressed in *E. coli* includes the following steps:

1. Preparation of Genomic DNA, Restriction Digestion and Construction of Genomic DNA Libraries Genomic DNA was prepared from *Pseudomonas putida* by the standard method. The genomic DNA was partially digested with NlaIII and completely digested with NsiI, PstI, AvrII, NheI, SpeI and XbaI. pJS105-22 was digested with either SphI, SbfI or XbaI followed by CIP treatment. NlaIII fragments were ligated into SphI digested vector. PstI and NsiI fragments were ligated into SbfI digested vector. AvrII, NheI, SpeI and XbaI fragments were ligated into XbaI digested vector. The ligated DNA was used to transform ER2502 by electroporation and the transformation mixes were plated at 30° C. on LB-agar plates containing chloramphenicol (Cam). Approximately 2000 transformants were obtained for each of the NlaIII, PstI, and NsiI libraries. Approximately 1200 transformants were obtained for each of the AvrII, NheI, SpeI and XbaI libraries. Seven individual libraries were prepared corresponding to each enzyme used to digest the genomic DNA. The primary libraries were prepared by pooling the transformants and inoculating 100 mL of LB broth supplemented with Cam and growing overnight at 30° C. to saturation. Plasmid DNA was isolated from 1.5 mL of the saturated culture.

2. Cloning of the ppuMIM Gene by Methylase Selection

The seven primary libraries were challenged (digested) with 40 units PpuMI restriction endonuclease for 4 hours at 37° C. The digested DNA was precipitated with ethanol and resuspended in distilled water. One-half of each challenged library (10 µL) was transformed into ER2502 competent cells. Each transformation mix was plated overnight at 30° C. on LB-Cam plates. Approximately 40–60 transformants were found on each plate except the PstI library resulted in only three transformants. Thirty-six clones were screened for presence of the ppuMIM gene by testing for resistance to PpuMI digestion. Ten of twelve NlaIII clones, four of four NsiI clones and eight of nine NheI clones were resistant to PpuMI digestion indicating the presence of a functional ppuMIM gene. Six of the inserts were sequenced from one end and NsiI clone 2A was found to carry a gene coding for a protein with similarity to the C5-cytosine DNA methyltransferase family and extensive similarity to the Eco109I methylase. The insert of clone 2A was further sequenced until the complete 1341 bp ORF was identified. This gene was named ppuMIM.

3. Restriction Mapping and Subcloning of the Insert

The 3' end of the ppuMIM gene was known from the initial sequencing of clone 2A. A SapI site is immediately downstream of the stop codon and is also present one time in vector pJS105-22. This rare cutting enzyme was used to estimate the size of insert 2A. Insert 2A was found to be approximately 5.2 kb. In order to subclone a smaller fragment into pSYX20, clone 2A was digested with several blunt cutting enzymes to find that SfoI cuts approximately 250 bp upstream of ppuMIM. The downstream cloning site was XbaI found in the polylinker of pJS105-22. Therefore, a 1.9 kb SfoI-XbaI ppuMIM fragment was cloned into the EcoRV-NheI sites of pSYX20 to give pSYX20-PpuMIM (clone X12).

4. Inverse PCR Amplification of DNA Downstream of PpuMI Methylase

After identification of the methylase gene, efforts were made to clone adjacent DNA. One truncated ORF was found downstream of the ppuMIM gene. DNA sequence following the C-terminus of the ppuMIM gene was used as the template for inverse PCR. The genomic DNA was digested with restriction enzymes, purified by Qiagen spin column, and self-ligated. The circular DNA molecules were used as templates for inverse PCR. PCR products greater than 1.0 kb were found in the BsaWI, RsaI, HaeII, NgoMIV and BsrFI templates. The 1.7 kb BsaWI PCR product was purified from a low-melting agarose gel, precipitated with ethanol, and sequenced directly with a primer used for the inverse PCR reaction. Using one additional primer, the BsaWI PCR fragment allowed the generation of 1440 bp of additional sequence. An open reading frame of either 975 or 1050 bp was identified within this downstream region corresponding to translational start at ATG or GTG, respectively. Eventually, the 1050 bp ORF beginning with GTG was confirmed as the ppuMIR gene encoding a protein of 349 amino acid residues. In the native strain ppuMIM and ppuMIR are transcribed in the same direction with only 17 bp separating the ppuMIM stop codon from the ppuMIR start codon (see FIG. 1 for gene organization).

5. Expression of PpuMIR Gene in *E. coli*

The successful cloning/expression strategy was to express the ppuMIR gene from the low copy vector pJS12T containing a p15A origin of replication, a tetracycline resistance gene, a Ptac promoter and a lacI gene. The *E. coli* host used for ppuMIR over-expression was ER2502 [pSYX20-PpuMIM]. Vector pSYX20 contains a pSC101 origin of replication and a kanamycin resistance gene. Complete methylation protection of ER2502 [pSYX20-PpuMIM] genomic DNA was inferred by isolating plasmid pSYX20-PpuMIM from ER2502 and confirming resistance to PpuMI digestion (pSYX20 contains one PpuMI site not blocked by dcm methylation).

Figure 4:
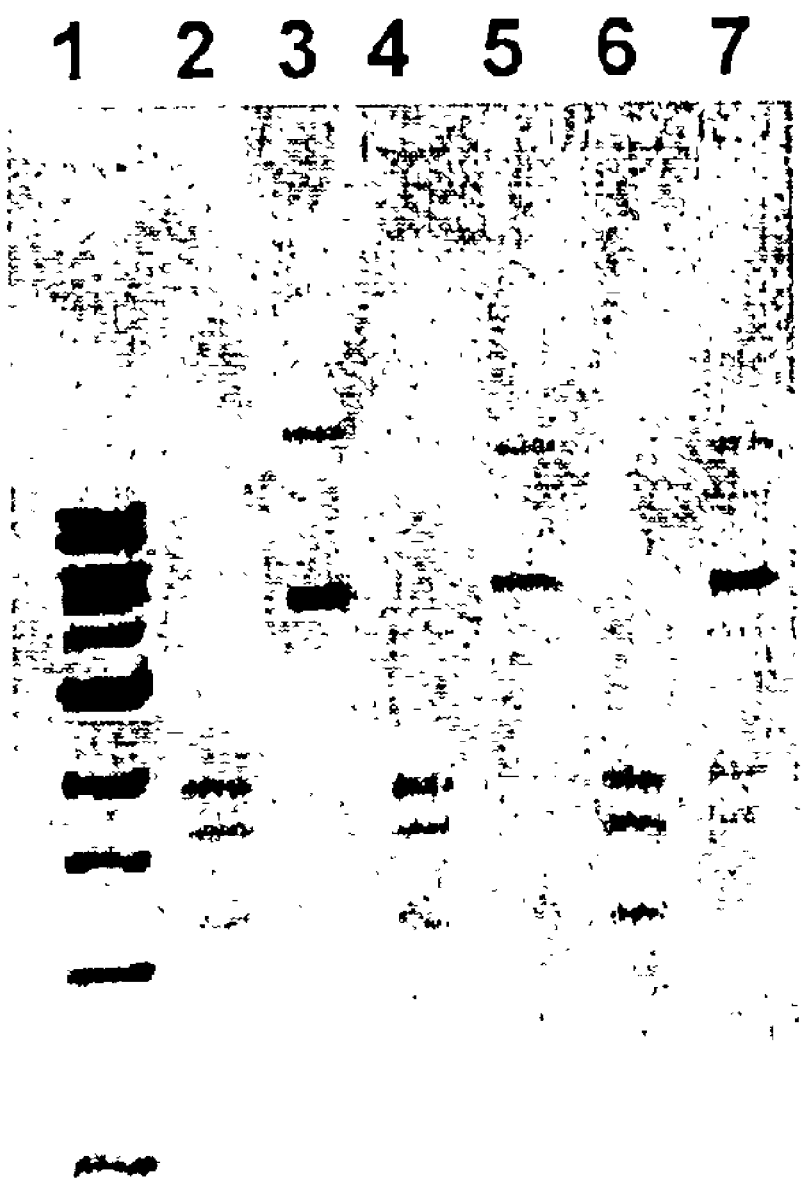
FIG. 4. Recombinant PpuMI endonuclease activity in cell extract. pJS105-22 DNA was used as the substrate. Lane 1, 1 kb DNA size marker. Lane 2, digestion with 4 units native PpuMI. Lane 3, pJS105-22 substrate (undigested). Lanes 4 and 5, digestion with 2 µl clone PP2 cell extract diluted 1:10 and 1:100, respectively. Lanes 6 and 7, digestion with 2 µl clone PP3 cell extract diluted 1:10 and 1:100, respectively.

The ppuMIR gene was amplified from genomic DNA by PCR using a mixture of Taq and Vent® DNA polymerase (5U/0.1U). Following purification and digestion with NdeI and EcoRI, the PCR fragment was ligated to CIP-treated pJS12T with compatible ends. The ligated DNA was transformed into pre-modified host ER2502 [pSYX20-PpuMIM]. Ten ml cell cultures were grown from individual transformants and the putative ppuMIR clones were induced with IPTG. Cell extracts were prepared and assayed for PpuMI endonuclease activity on DNA substrate pJS105-22. Ten highly active PpuMI-producing clones were found after screening fourteen IPTG-induced cell extracts. The PpuMI activity of two clones is shown in FIG. 4. The cell extracts of clones PP2 and PP3 both provide complete digestion at a 1:10 dilution and partial digestion at a 1:100 dilution. The recombinant PpuMI endonuclease yield was $2.4 \times 10^5$ units/ gram of wet cells. The recombinant PpuMI-overproducing strain consists of ER2502 harboring plasmids pJS12T-PpuMIR and pSYX20-PpuMIM. The PpuMI-overproducing strain was tested for plasmid stability and tolerance to extended induction of ppuMIR. A single colony was grown for multiple generations to simulate production conditions. At the point of IPTG induction (200 Klett units), an aliquot of cells was plated on LB-agar versus LB-agar plus 15 µg/ml Tet and 50 µg/ml Kan. The number of colonies on each plate was similar, thus indicating plasmid stability. Furthermore, cell culture induced for ppuMIR expression for 3, 4.5 or 16 hours at 37° C. resulted in a similar yield of PpuMI units.

The plasmid DNA pJS12T-PpuMIR (clone PP3) was prepared by Qiagen column and the entire insert was sequenced. The DNA sequence of clone PP3 was confirmed to be wild-type as it matched the sequence obtained from inverse PCR of *Pseudomonas putida* genomic DNA.

The references cited above and below are herein incorporated by reference.

The present invention is further illustrated by the following Example. This Example is provided to aid in the understanding of the invention and is not construed as a limitation thereof.

EXAMPLE 1

Cloning of PpuMI Restriction-Modification System in *E. coli*

1. Preparation of Genomic DNA

Genomic DNA was prepared from 4.4 g of *Pseudomonas putida* (NEB#372, New England Biolabs, Beverly, Mass.) by the standard procedure consisting of the following steps:

(a) Cell lysis by resuspending cells in 20% sucrose, 50 mM Tris-HCl (pH 8.0), 0.1 M EDTA and addition of lysozyme (1.7 mg/ml final conc.);

(b) Further cell lysis by addition of SDS at a final concentration of 1.0%;

(c) Further cell lysis by addition of 1% Triton X-100, 62 mM EDTA, 50 mM Tris-HCl, pH 8.0 to give a final conc. of 0.1% Triton X-100;

(d) Addition of 70 ml TE (pH 8.0) to improve DNA extraction;

(e) Removal of proteins by phenol-$CHCl_3$ extraction twice (equal volume) and $CHCl_3$ extraction once (equal volume);

(f) Dialysis in 4 liters of TE buffer, buffer change twice;

(g) RNase A treatment to remove RNA (0.1 mg/ml final conc.);

(h) Genomic DNA precipitation with 0.1 volume 3 M sodium acetate (pH 5.2) and 1.0 volume isopropanol, followed by 70% cold ethanol wash of the pellet; and (i) Final genomic DNA resuspension in 4 ml TE to a final concentration of 0.5 mg/ml.

2. Construction of PpuMI Methylase Selection Vector pJS105-22.

Vector pUC18 was modified as follows: The RNA II primer promoter essential for replication was exchanged for a promoter containing a PpuMI site between the −35 and −10 contact sites for *E. coli* RNA polymerase. To enable promoter exchange, a unique BglII site was created at position −44 relative to the transcription start site for the RNA II primer. In addition, an NgoMIV site was created at the transcription start site. Finally, two complementary phosphorylated oligonucleotides were ligated into the BglII/NgoMIV digested, CIP-treated vector to create a PpuMI site (AG/GTCCT) at −17 to −23. The modified promoter is shown below (mutated positions are in bold, the restriction sites are underlined):

(SEQ ID NO:5)
5'<u>agatct</u>tcttgagatccttt<b>aggtcct</b>gcgtaatctgct<u>gccggc</u>3'

The modified vector exhibited a copy number equal to or slightly greater than the wild-type pUC18 copy number. Next, the yidC gene (HindIII/XmnI) of *E. coli* was cloned into the HindIII/SfoI sites to create the final vector, pJS105-22. The yidC gene provides two additional PpuMI sites to reduce the number of false positives during the methylase selection procedure. An important note is that the yidC gene product is lethal to *E. coli* when cells carrying pJS105-22 are grown at 37° C. Therefore, cells carrying pJS105-22 must be grown at 30° C. to reduce the plasmid copy number and, in turn, reduce the cellular concentration of the yidC gene product.

3. Restriction Digestion of Genomic DNA and Construction of Genomic DNA Libraries Varying amounts of NlaIII (6, 1.25 and 0.375 units) were used to digest 20 µg genomic DNA for 30 min at 37° C. to achieve limited partial digestion. The partially digested DNA from the 1.25 unit reaction was separated on a 1% low-melting agarose gel and the DNA fragments of 2–10 kb were excised. After β-agarase treatment and ethanol precipitation, the DNA fragments were ligated into pJS105-22 prepared by SphI digestion and CIP treatment. In addition, genomic DNA (20 µg each reaction) was completely digested with NsiI, PstI, AvrII, NheI, SpeI or XbaI. Fragments of 2–10 kb were isolated as described above. The NsiI and PstI fragments were ligated into SbfI digested, CIP-treated vector. AvrII, NheI, SpeI and XbaI fragments were ligated into XbaI digested, CIP-treated vector. The ligated DNA was used to transform endA⁻ RR1 competent cells (ER2502, New England Biolabs, Beverly, Mass.) by electroporation. The transformation mixes were plated at 30° C. on LB-agar plates containing chloramphenicol (Cam). Approximately 2000 transformants were obtained for each of the NlaIII, PstI, and NsiI libraries. Approximately 1200 transformants were obtained for each of the AvrII, NheI, SpeI and XbaI libraries. Seven individual libraries were prepared corresponding to each enzyme used to digest the genomic DNA. Each library was prepared by pooling the colonies, inoculating 100 ml LB+Cam, growing overnight at 30° C. to saturation and isolating plasmid from 1.5 ml of the saturated culture.

4. Cloning of ppuMIM Gene by Methylase Selection

The primary plasmid DNA libraries (from 1.5 ml saturated culture) were challenged (digested) with 40 units of PpuMI for 4 hours at 37° C. The digested DNA was ethanol precipitated and resuspended in 20 µl distilled water. One-half of each library (10 µl) was transformed into ER2502. Each transformation mix was plated overnight at 30° C. on LB-Cam plates. Approximately 40–60 transformants were found on each plate except the PstI library resulted in only three transformants. Thirty-six clones were screened for presence of the ppuMIM gene by testing for resistance to PpuMI digestion. Ten of twelve NlaIII clones, four of four NsiI clones and eight of nine NheI clones were resistant to PpuMI digestion indicating the presence of a functional ppuMIM gene. Six of the inserts were sequenced from one end using a pUC universal primer (NEB#s1233s; New England Biolabs, Beverly, Mass.). DNA sequencing was performed using the dye terminator sequencing kit from PE Biosystems. NsiI clone 2A was found to carry a gene coding for a protein with similarity to the C5-cytosine DNA methyltransferase family and extensive similarity to the Eco109I methylase. The insert of clone 2A was further sequenced using custom-made primers until the complete 1341 bp ORF was identified. This gene was named ppuMIM.

5. Restriction Mapping of ppuMIM Clones and Analysis for Simultaneous Cloning of ppuMIR.

The 3' end of the ppuMIM gene was known from the initial sequencing of clone 2A. A SapI site is immediately downstream of the stop codon and is also present one time in vector pJS105-22. This rare cutting enzyme was used to estimate the size of insert 2A. Insert 2A was found to be approximately 5.2 kb. The inserts of three other clones were mapped to determine the orientation of each. Clone NlaIII 1D contained a 3.7 kb insert, clone NlaIII 1J contained a 4.0 kb insert, and clone NheI 5A contained a 4.5 kb insert. SapI mapping indicated that in all four clones, only a short Pseudomonas putida DNA segment was present downstream of ppuMIM. This result indicated that the ppuMIR gene most likely resides downstream of ppuMIM as simultaneous cloning of methylase and endonuclease genes is rare due to the need for pre-protection of host cells. However, the first attempt at cloning the adjacent downstream ORF (beginning with ATG) resulted in no detectable PpuMI endonuclease activity. Therefore, the cell extract of all four original clones 2A, 1D, 1J and 5A was analyzed for PpuMI endonuclease activity as all four clones carry greater than 1 kb of sequence upstream of ppuMIM. Again, the result was negative for PpuMI endonuclease activity. Finally, DNA rearrangement upstream of ppuMIM was ruled out in clones 2A and 5A by PCR amplification of a 1.2 kb fragment equivalent to a 1.2 kb fragment amplified from Pseudomonas putida genomic DNA using primers 279-123 and 279-124. In the absence of DNA rearrangement upstream of ppuMIM, it was again concluded that the ppuMIR gene most likely resides downstream of ppuMIM. At this point, the putative GTG start codon was discovered only 17 bp downstream of ppuMIM.

5'cgctgtaactcgacatgctctgtc3' (279-123)(SEQ ID NO: 6) (reverse primer that anneals to ppuMIM start site)

5'gactacggttgcgcagtcgag3' (279-124) (SEQ ID NO: 7) (ppuMIM upstream primer known from initial 5A sequencing)

6. Sequencing of the ppuMIM Upstream Region to Rule Out the Presence of ppuMIR

Clones 2A and 5A were sequenced using primers 279-123 and 279-124 (see above) to identify any putative ORFs within the 1.2 kb DNA segment upstream of ppuMIM. One ORF was found 600 bp upstream of ppuMIM but the hypothetical protein sequence displayed similarity to transposase proteins of various bacteria.

7. Subcloning of the ppuMIM Gene.

In order to subclone a smaller fragment containing ppuMIM, clone 2A was digested with several blunt cutting enzymes to find that SfoI cuts approximately 250 bp upstream of ppuMIM. The downstream cloning site was XbaI found in the polylinker of pJS105-22. Therefore, a 1.9 kb SfoI-XbaI ppuMIM fragment was excised from clone 2A and cloned into the EcoRV-NheI sites of pSYX20 to give pSYX20-PpuMIM (clone X12). Clone X12 was confirmed to carry the ppuMIM gene by testing for resistance to PpuMI digestion. (pSYX20 contains one PpuMI site not blocked by dcm methylation).

8. Inverse PCR Amplification of DNA Downstream of ppuMIM

After identification of the methylase gene, efforts were made to clone downstream DNA. One truncated ORF was found downstream of the ppuMIM gene. DNA sequence following the C-terminus of the ppuMIM gene was used as the template for inverse PCR primer design.

Two primers were synthesized with the following sequences:

5'ttcaccagtccgtatgtcttgctg3' (276-178) (SEQ ID NO: 8)

5'ggcatcggcagcggttagggatcc3' (276-179) (SEQ ID NO: 9)

The genomic DNA was digested with 16 restriction enzymes with sites known to be present near the inverse PCR priming sites. The digested DNA was purified by Qiagen spin column, and self-ligated at a low concentration (4 µg/ml) overnight at 16° C. T4 DNA ligase was inactivated at 65° C. for 20 min and the circular DNA molecules were used as templates for inverse PCR. PCR conditions were 94° C. for 3 min (1 cycle); 94° C. for 30 sec, 55° C. for 1 min, 72° C. for 2 min (35 cycles). PCR products greater than 1.0 kb were found in the BsaWI, RsaI, HaeII, NgoMIV and BsrFI templates. The 1.7 kb BsaWI PCR product was purified from a low-melting agarose gel, precipitated with ethanol, and sequenced directly with primer 276-178. Using one additional primer (277-245), the BsaWI PCR fragment allowed the generation of 1440 bp of additional downstream sequence. Initially, an open reading frame of 975 bp beginning with ATG was identified starting 92 bp downstream of ppuMIM.

5'tcagcgtagtcagatagcat3' (SEQ ID NO: 10) (277-245, anneals within ppuMIR to complete sequencing)

9. Modification of pR976 to Create Expression Vector pJS12T.

Figure 5:
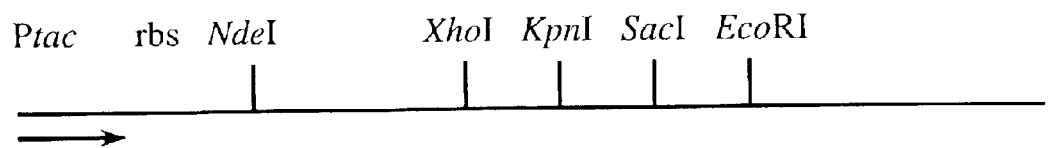
FIG. 5. The promoter and cloning sites of ppuMIR expression vector pJS12T created by modification of pR976 (NEB collection; New England Biolabs, Beverly, Mass.). Unique cloning sites are indicated. rbs, ribosome binding site sequence gaagga.

The putative ppuMIR gene contained an internal NcoI site, which disallowed cloning of the gene into pR976 (NEB collection). Therefore, pR976 was modified to create an NdeI site at the translational start site. The NcoI site present in pR976 was destroyed by the modification. The promoter and cloning sites of pJS12T are shown in FIG. 5. Desirable features of pJS12T (and pR976) include a Ptac promoter, the lacI gene, a tetracycline resistance gene, and a low-copy p15A origin of replication. These features make pJS12T (and pR976) ideal for expression of restriction endonuclease genes in two plasmid systems where the methylase gene is carried by a plasmid with either a pSC101 or ColE1-type origin of replication.

10. Cloning of the 975 bp ORF Downstream of ppuMIM to Identify ppuMIR

Type II endonuclease genes commonly do not exhibit homology to any other members of the endonuclease family. In some cases, two proteins with identical or nearly identical recognition sequences will possess similarity at the protein level. In this case, the 975 bp ORF downstream of ppuMIM did not display any similarity to the Eco109I restriction endonuclease (recognition site RG/GNCCY, whereas PpuMI recognizes RG/GWCCY). Therefore, identification of ppuMIR required cloning into a pre-modified host and analysis of the cell extract for endonuclease activity.

Two PCR primers were synthesized for PCR amplification of the 975 bp ORF from *Pseudomonas putida* genomic DNA:

```
                                       (SEQ ID NO:11)
5'caccaccaccatatggctgttgatctcgacccgagt3'
(278-196, underlined nt, NdeI site)

(SEQ ID NO:12)
5' caccaagaattctaggggagtcgaacc 3'
(278-195, underlined nt, EcoRI site)
```

PCR conditions were 94° C. for 3 min (1 cycle); 94° C. for 30 sec, 55° C. for 1 min, 72° C. for 2 min (22 cycles). The PCR product was purified by Qiagen spin column, digested with NdeI and EcoRI at 37° C., purified by excision from a low-melt agarose gel and ligated to CIP treated pJS12T with compatible ends. Following a 10 min ligation with the Quick Ligation™ kit (New England Biolabs; Beverly, Mass.), the DNA was transferred into ER2502 [pSYX20-PpuMIM] by transformation. Fourteen recombinant clones were analyzed for PpuMI activity by growing 10 ml cultures, inducing with 0.5 mM IPTG for 3 hours and preparing cell extract from each of the induced cultures. PpuMI activity was not detected in any of the fourteen cell extracts. Therefore, the 975 bp downstream ORF (beginning with ATG) does not encode an active PpuMI endonuclease.

11. Cloning of the 1050 bp ORF Downstream of ppuMIM to Identify ppuMIR

In some cases, bacterial protein translation has been shown to initiate via recognition of a codon other than AUG. Specifically, GUG (which codes for valine) can be used to initiate protein translation in some bacteria. With respect to the present invention, a GTG sequence was found only 17 bp downstream of ppuMIM and this GTG was in-frame with respect to the 975 bp ORF. Initiation of protein translation at this position in *Pseudomonas putida* would produce a protein of 349 amino acid residues, encoded by an ORF of 1050 bp. To test this possibility, the 1050 bp ORF was amplified from *Pseudomonas putida* genomic DNA using primer 280-29 (listed below) and primer 278-195 (listed above). Primer 280-29 anneals at the GTG start site for the putative ppuMIR gene and creates a point mutation to provide an ATG rather than GTG for greater expression in the recombinant clone. Primer 278-195 anneals downstream of the putative ppuMIR gene.

```
                                       (SEQ ID NO:13)
5'caccaccaccatatggcaaaagggcatccaggactac3'
(280-29, underlined nt, NdeI site)
```

PCR conditions were 94° C. for 3 min (1 cycle); 94° C. for 30 sec, 55° C. for 1 min, 72° C. for 2 min (22 cycles). The PCR product was purified by Qiagen spin column, digested with NdeI and EcoRI at 37° C., purified by excision from a low-melt agarose gel and ligated to CIP treated pJS12T with compatible ends. Following a 10 min ligation with the Quick Ligation™ kit (New England Biolabs, Beverly, Mass.), the DNA was transferred into ER2502 [pSYX20-PpuMIM] by transformation. Fourteen recombinant clones were analyzed for PpuMI activity by growing 10 ml cultures, inducing with 0.5 mM IPTG for 3 hours and preparing cell extract from each of the induced cultures. PpuMI activity was detected in ten of the fourteen cell extracts. The endonuclease activity of clones PP2 and PP3 is displayed in FIG. 4. The cell extracts of clones PP2 and PP3 both provide complete digestion at a 1:10 dilution and partial digestion at a 1:100 dilution indicating overproduction of PpuMI. The recombinant PpuMI endonuclease yield was $2.4 \times 10^5$ units/gram of wet cells. The recombinant PpuMI-overproducing strain consists of ER2502 harboring plasmids pJS12T-PpuMIR and pSYX20-PpuMIM.

The 1050 bp downstream ORF (beginning with GTG in the native strain) encodes the active PpuMI endonuclease. Transcription of ppuMIM and ppuMIR genes is oriented in the same direction in *Pseudomonas putida*. They are arranged in head-to-tail fashion separated by 17 bp (see FIG. 1 for gene organization).

The plasmid DNA pJS12T-PpuMIR (clone PP3) was prepared by Qiagen column and the entire insert was sequenced. The DNA sequence of clone PP3 was confirmed to be wild-type as it matched the sequence obtained from inverse PCR of *Pseudomonas putida* genomic DNA.

The strain NEB#1461, ER2502 [pJS12T-PpuMIR, pSYX20-PpuMIR] has been deposited under the terms and conditions of the Budapest Treaty with the American Type Culture Collection on May 17, 2002 and received ATCC Accession No. PTA-4373.

What is claimed is:

1. Isolated DNA encoding the PpuMI restriction endonuclease, wherein the isolated DNA is obtainable from *Pseudomonas putida*.

2. A recombinant DNA vector comprising a vector into which a DNA segment encoding the PpuMI restriction endonuclease has been inserted.

3. Isolated DNA encoding the PpuMI restriction endonuclease and PpuMI methylase, wherein the isolated DNA is obtainable from ATCC No. PTA-4373.

4. Vectors that comprise the isolated DNA of claim 3.

5. A host cell transformed by the vector of claim 2 or 4.

6. A method of producing recombinant PpuMI restriction endonuclease comprising culturing a host cell transformed with the vector of claim 2 or 4 under conditions suitable for expression of said endonuclease.

* * * * *

SEQUENCE LISTING

<160> NUMBER OF SEQ ID NOS: 13

<210> SEQ ID NO 1
<211> LENGTH: 1341
<212> TYPE: DNA
<213> ORGANISM: Pseudomonas putida Methylase gene sequence
<220> FEATURE:
<221> NAME/KEY: CDS
<222> LOCATION: (1)..(1341)
<223> OTHER INFORMATION:

<400> SEQUENCE: 1

| | | | | | | | | | | | | | | | | |
|---|---|---|---|---|---|---|---|---|---|---|---|---|---|---|---|---|
| atg | agt | cag | aaa | aag | cta | aaa | gtg | ata | tct | ctg | ttt | tca | ggg | ggg | atg | 48 |
| Met | Ser | Gln | Lys | Lys | Leu | Lys | Val | Ile | Ser | Leu | Phe | Ser | Gly | Gly | Met | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggc | cta | gac | ctt | ggc | ctc | aaa | gag | act | gaa | aga | tac | gaa | ctt | cta | gca | 96 |
| Gly | Leu | Asp | Leu | Gly | Leu | Lys | Glu | Thr | Glu | Arg | Tyr | Glu | Leu | Leu | Ala | |
| | | 20 | | | | | 25 | | | | | 30 | | | | |

| | | | | | | | | | | | | | | | | |
|---|---|---|---|---|---|---|---|---|---|---|---|---|---|---|---|---|
| tgt | gtt | gag | aaa | gtt | cca | gct | tac | tgc | gaa | acg | atc | cgt | ctt | aat | aga | 144 |
| Cys | Val | Glu | Lys | Val | Pro | Ala | Tyr | Cys | Glu | Thr | Ile | Arg | Leu | Asn | Arg | |
| | | 35 | | | | | 40 | | | | | 45 | | | | |

| | | | | | | | | | | | | | | | | |
|---|---|---|---|---|---|---|---|---|---|---|---|---|---|---|---|---|
| gac | gcc | ggt | cgc | cta | cct | gca | ggt | atg | aaa | ctc | tat | gag | ggc | gac | atc | 192 |
| Asp | Ala | Gly | Arg | Leu | Pro | Ala | Gly | Met | Lys | Leu | Tyr | Glu | Gly | Asp | Ile | |
| 50 | | | | | 55 | | | | | 60 | | | | | | |

| | | | | | | | | | | | | | | | | |
|---|---|---|---|---|---|---|---|---|---|---|---|---|---|---|---|---|
| acg | aat | gtt | gac | cct | tat | gat | gtt | atg | gcc | gca | act | gga | att | aag | ccc | 240 |
| Thr | Asn | Val | Asp | Pro | Tyr | Asp | Val | Met | Ala | Ala | Thr | Gly | Ile | Lys | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggt | gag | ctt | gac | gta | ttg | gta | ggg | ggg | cca | cct | tgc | caa | tca | ttt | agc | 288 |
| Gly | Glu | Leu | Asp | Val | Leu | Val | Gly | Gly | Pro | Pro | Cys | Gln | Ser | Phe | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | gct | ggc | aat | cgg | ggg | acc | gta | caa | gac | cct | cgg | ggt | act | ctg | ctg | 336 |
| Thr | Ala | Gly | Asn | Arg | Gly | Thr | Val | Gln | Asp | Pro | Arg | Gly | Thr | Leu | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| tgg | caa | ttc | cta | aag | ttt | gtt | gaa | gtc | ctt | cag | cca | aag | ttc | ttc | ctg | 384 |
| Trp | Gln | Phe | Leu | Lys | Phe | Val | Glu | Val | Leu | Gln | Pro | Lys | Phe | Phe | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| atg | gag | aac | gta | cgt | gga | ttg | att | tct | gct | gca | ctg | agg | cat | cgc | ccc | 432 |
| Met | Glu | Asn | Val | Arg | Gly | Leu | Ile | Ser | Ala | Ala | Leu | Arg | His | Arg | Pro | |
| | | 130 | | | | | 135 | | | | | 140 | | | | |

| | | | | | | | | | | | | | | | | |
|---|---|---|---|---|---|---|---|---|---|---|---|---|---|---|---|---|
| att | gct | gag | cgc | cct | cca | aaa | ggt | cca | gag | cta | tca | gtt | gat | gaa | atg | 480 |
| Ile | Ala | Glu | Arg | Pro | Pro | Lys | Gly | Pro | Glu | Leu | Ser | Val | Asp | Glu | Met | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cct | gga | tca | gtc | att | cgg | cta | ttc | tct | caa | gat | ctc | cag | aga | ctt | gaa | 528 |
| Pro | Gly | Ser | Val | Ile | Arg | Leu | Phe | Ser | Gln | Asp | Leu | Gln | Arg | Leu | Glu | |
| | | | | 165 | | | | | 170 | | | | | 175 | | |

| | | | | | | | | | | | | | | | | |
|---|---|---|---|---|---|---|---|---|---|---|---|---|---|---|---|---|
| gcc | aag | tac | cat | ctg | gat | gta | ttc | gag | gta | aac | tcc | gtt | aat | tac | gga | 576 |
| Ala | Lys | Tyr | His | Leu | Asp | Val | Phe | Glu | Val | Asn | Ser | Val | Asn | Tyr | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| gct | cct | caa | att | cgt | gag | cga | gtc | ctt | ttc | ata | gga | aat | cgt | ttt | ggg | 624 |
| Ala | Pro | Gln | Ile | Arg | Glu | Arg | Val | Leu | Phe | Ile | Gly | Asn | Arg | Phe | Gly | |
| | | 195 | | | | | 200 | | | | | 205 | | | | |

| | | | | | | | | | | | | | | | | |
|---|---|---|---|---|---|---|---|---|---|---|---|---|---|---|---|---|
| gca | cag | gtc | gcg | ttc | cca | gat | cca | acc | cac | ggc | cct | gta | gat | ggg | ttg | 672 |
| Ala | Gln | Val | Ala | Phe | Pro | Asp | Pro | Thr | His | Gly | Pro | Val | Asp | Gly | Leu | |
| | | 210 | | | | | 215 | | | | | 220 | | | | |

| | | | | | | | | | | | | | | | | |
|---|---|---|---|---|---|---|---|---|---|---|---|---|---|---|---|---|
| gat | gca | gaa | gat | gat | ctc | ttt | ggc | aca | agc | tca | aag | ctc | aaa | ggc | tgg | 720 |
| Asp | Ala | Glu | Asp | Asp | Leu | Phe | Gly | Thr | Ser | Ser | Lys | Leu | Lys | Gly | Trp | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cgc | tcc | ttg | ggt | gac | gtg | ata | tct | gat | ctt | cat | gag | atc | gca | cct | gag | 768 |
| Arg | Ser | Leu | Gly | Asp | Val | Ile | Ser | Asp | Leu | His | Glu | Ile | Ala | Pro | Glu | |
| | | | | 245 | | | | | 250 | | | | | 255 | | |

```
att atg gac ttc agc cca agg aag aaa tct ttc ctt gag atg gtt cca      816
Ile Met Asp Phe Ser Pro Arg Lys Lys Ser Phe Leu Glu Met Val Pro
        260                 265                 270 gag ggt tca aac tgg cga agt ctg cca gaa gaa att caa aag gaa tca      864
Glu Gly Ser Asn Trp Arg Ser Leu Pro Glu Glu Ile Gln Lys Glu Ser
            275                 280                 285 atg gga aag gcc tgg ctg gcg aaa ggg ggg cgg tct ggt tgg tgg agg      912
Met Gly Lys Ala Trp Leu Ala Lys Gly Gly Arg Ser Gly Trp Trp Arg
290                 295                 300 aga ctt acc atg gac ctc cca tgc ccc act ctg gta acg atg cca aat      960
Arg Leu Thr Met Asp Leu Pro Cys Pro Thr Leu Val Thr Met Pro Asn
305                 310                 315                 320 cac tca agt aca tca ctg tgc cat ccg gtg cat act cga gcg ctc tct     1008
His Ser Ser Thr Ser Leu Cys His Pro Val His Thr Arg Ala Leu Ser
                325                 330                 335 gtg agg gaa tat gcg cga att caa gag ttc cct gat tac tgg gag ttc     1056
Val Arg Glu Tyr Ala Arg Ile Gln Glu Phe Pro Asp Tyr Trp Glu Phe
            340                 345                 350 gca gga aaa atc gcc gat aaa tat gcg cag ata gga aat gct gtg ccc     1104
Ala Gly Lys Ile Ala Asp Lys Tyr Ala Gln Ile Gly Asn Ala Val Pro
        355                 360                 365 gtg agg tta ggc aaa gta gcc ggc gag gtg att gca aag tgc tat gat     1152
Val Arg Leu Gly Lys Val Ala Gly Glu Val Ile Ala Lys Cys Tyr Asp
370                 375                 380 gag cta cag gcg aat ggg tgg ctg cct ctg gcg cag gct ccc gaa gct     1200
Glu Leu Gln Ala Asn Gly Trp Leu Pro Leu Ala Gln Ala Pro Glu Ala
385                 390                 395                 400 ttc agg atc gtt tat ata cag tct cat gtg cgt act cga cgt tgg ttc     1248
Phe Arg Ile Val Tyr Ile Gln Ser His Val Arg Thr Arg Arg Trp Phe
                405                 410                 415 aaa gac ggc aaa aca att gtc tgg gat aaa gaa act gac gaa gcg gac     1296
Lys Asp Gly Lys Thr Ile Val Trp Asp Lys Glu Thr Asp Glu Ala Asp
            420                 425                 430 tac gga cag tca aaa acc aag cgc ctt gtg aag gcc ttg gct taa         1341
Tyr Gly Gln Ser Lys Thr Lys Arg Leu Val Lys Ala Leu Ala
        435                 440                 445

<210> SEQ ID NO 2
<211> LENGTH: 446
<212> TYPE: PRT
<213> ORGANISM: Pseudomonas putida Methylase gene sequence

<400> SEQUENCE: 2

Met Ser Gln Lys Lys Leu Lys Val Ile Ser Leu Phe Ser Gly Gly Met
1               5                   10                  15

Gly Leu Asp Leu Gly Leu Lys Glu Thr Glu Arg Tyr Glu Leu Leu Ala
            20                  25                  30

Cys Val Glu Lys Val Pro Ala Tyr Cys Glu Thr Ile Arg Leu Asn Arg
        35                  40                  45

Asp Ala Gly Arg Leu Pro Ala Gly Met Lys Leu Tyr Glu Gly Asp Ile
    50                  55                  60

Thr Asn Val Asp Pro Tyr Asp Val Met Ala Ala Thr Gly Ile Lys Pro
65                  70                  75                  80

Gly Glu Leu Asp Val Leu Val Gly Gly Pro Pro Cys Gln Ser Phe Ser
                85                  90                  95

Thr Ala Gly Asn Arg Gly Thr Val Gln Asp Pro Arg Gly Thr Leu Leu
            100                 105                 110

Trp Gln Phe Leu Lys Phe Val Glu Val Leu Gln Pro Lys Phe Phe Leu
```

```
                115                 120                 125
Met Glu Asn Val Arg Gly Leu Ile Ser Ala Ala Leu Arg His Arg Pro
            130                 135                 140
Ile Ala Glu Arg Pro Pro Lys Gly Pro Glu Leu Ser Val Asp Glu Met
145                 150                 155                 160
Pro Gly Ser Val Ile Arg Leu Phe Ser Gln Asp Leu Gln Arg Leu Glu
                165                 170                 175
Ala Lys Tyr His Leu Asp Val Phe Glu Val Asn Ser Val Asn Tyr Gly
            180                 185                 190
Ala Pro Gln Ile Arg Glu Arg Val Leu Phe Ile Gly Asn Arg Phe Gly
        195                 200                 205
Ala Gln Val Ala Phe Pro Asp Pro Thr His Gly Pro Val Asp Gly Leu
    210                 215                 220
Asp Ala Glu Asp Asp Leu Phe Gly Thr Ser Ser Lys Leu Lys Gly Trp
225                 230                 235                 240
Arg Ser Leu Gly Asp Val Ile Ser Asp Leu His Glu Ile Ala Pro Glu
                245                 250                 255
Ile Met Asp Phe Ser Pro Arg Lys Lys Ser Phe Leu Glu Met Val Pro
            260                 265                 270
Glu Gly Ser Asn Trp Arg Ser Leu Pro Glu Glu Ile Gln Lys Glu Ser
        275                 280                 285
Met Gly Lys Ala Trp Leu Ala Lys Gly Gly Arg Ser Gly Trp Trp Arg
    290                 295                 300
Arg Leu Thr Met Asp Leu Pro Cys Pro Thr Leu Val Thr Met Pro Asn
305                 310                 315                 320
His Ser Ser Thr Ser Leu Cys His Pro Val His Thr Arg Ala Leu Ser
                325                 330                 335
Val Arg Glu Tyr Ala Arg Ile Gln Glu Phe Pro Asp Tyr Trp Glu Phe
            340                 345                 350
Ala Gly Lys Ile Ala Asp Lys Tyr Ala Gln Ile Gly Asn Ala Val Pro
        355                 360                 365
Val Arg Leu Gly Lys Val Ala Gly Glu Val Ile Ala Lys Cys Tyr Asp
    370                 375                 380
Glu Leu Gln Ala Asn Gly Trp Leu Pro Leu Ala Gln Ala Pro Glu Ala
385                 390                 395                 400
Phe Arg Ile Val Tyr Ile Gln Ser His Val Arg Thr Arg Arg Trp Phe
                405                 410                 415
Lys Asp Gly Lys Thr Ile Val Trp Asp Lys Glu Thr Asp Glu Ala Asp
            420                 425                 430
Tyr Gly Gln Ser Lys Thr Lys Arg Leu Val Lys Ala Leu Ala
        435                 440                 445

<210> SEQ ID NO 3
<211> LENGTH: 1050
<212> TYPE: DNA
<213> ORGANISM: Pseudomonas putida endonuclease gene sequence
<220> FEATURE:
<221> NAME/KEY: CDS
<222> LOCATION: (1)..(1050)
<223> OTHER INFORMATION:

<400> SEQUENCE: 3 atg gca aaa ggg cat cca gga cta ccc aaa ccg aac gtc gtt act ttc        48
Met Ala Lys Gly His Pro Gly Leu Pro Lys Pro Asn Val Val Thr Phe
1               5                   10                  15 tcg aag agt gag cta ctc gag caa cta atg gct gtt gat ctc gac ccg        96
```

```
                                                                    -continued Ser Lys Ser Glu Leu Leu Glu Gln Leu Met Ala Val Asp Leu Asp Pro
        20                  25                  30 agt gct aga gca aga gct ctt gct atg gaa gag caa ttc cgg aga aag      144
Ser Ala Arg Ala Arg Ala Leu Ala Met Glu Glu Gln Phe Arg Arg Lys
            35                  40                  45 atc gat tcg cac gtg gga tcc cta acc gct gcc gat gcc aaa ttt aat      192
Ile Asp Ser His Val Gly Ser Leu Thr Ala Ala Asp Ala Lys Phe Asn
 50                  55                  60 aag ttt ttc acc agt ccg tat gtc ttg ctg atg cat gct cga aaa aat      240
Lys Phe Phe Thr Ser Pro Tyr Val Leu Leu Met His Ala Arg Lys Asn
 65              70                  75                  80 cgc tac aca aga gtt agc gag atc gag cat gac atc ctt cct gca aag      288
Arg Tyr Thr Arg Val Ser Glu Ile Glu His Asp Ile Leu Pro Ala Lys
                85                  90                  95 cta ttt tcg tcc atg gaa acc tct gct ggt aga gcg gta gaa att atc      336
Leu Phe Ser Ser Met Glu Thr Ser Ala Gly Arg Ala Val Glu Ile Ile
            100                 105                 110 gca ctt cca gta tac gga tgg act cct gtc gta agc gca atg cac tct      384
Ala Leu Pro Val Tyr Gly Trp Thr Pro Val Val Ser Ala Met His Ser
        115                 120                 125 gca aat tct gct ctt gac ggg ctg cgc gtg aat ggc gat aca ctt cag      432
Ala Asn Ser Ala Leu Asp Gly Leu Arg Val Asn Gly Asp Thr Leu Gln
130                 135                 140 gtt gcg act tta aag agt ggt ccg cgc tgc ctg aat gat gag atg agc      480
Val Ala Thr Leu Lys Ser Gly Pro Arg Cys Leu Asn Asp Glu Met Ser
145                 150                 155                 160 gag aat ttc gca gat acc att att gca aat ctc gag gcc tgg gct aat      528
Glu Asn Phe Ala Asp Thr Ile Ile Ala Asn Leu Glu Ala Trp Ala Asn
                165                 170                 175 cag cat gat gtg cgg aaa gtg gag ttt acc tat ggg gtt cta tat gga      576
Gln His Asp Val Arg Lys Val Glu Phe Thr Tyr Gly Val Leu Tyr Gly
            180                 185                 190 act caa aag gtt tcg aat aag aaa gat tgg cac ata ttc aag aac ctc      624
Thr Gln Lys Val Ser Asn Lys Lys Asp Trp His Ile Phe Lys Asn Leu
        195                 200                 205 gct ttg aaa tta ccc gag ggc agt ttt tcc gtc ctc ccc aat gga cgc      672
Ala Leu Lys Leu Pro Glu Gly Ser Phe Ser Val Leu Pro Asn Gly Arg
    210                 215                 220 tgg gat tgc agt ttc gca tac aaa ggc att gaa gta gag gct ggg att      720
Trp Asp Cys Ser Phe Ala Tyr Lys Gly Ile Glu Val Glu Ala Gly Ile
225                 230                 235                 240 cgg atc gga aaa gat tgg tgg act cat cta ggt ggg aga ttg gga ttg      768
Arg Ile Gly Lys Asp Trp Trp Thr His Leu Gly Gly Arg Leu Gly Leu
                245                 250                 255 gcg gag cta gca att gcc cta atc cgt gct tgc atc gcg ccc ggt gat      816
Ala Glu Leu Ala Ile Ala Leu Ile Arg Ala Cys Ile Ala Pro Gly Asp
            260                 265                 270 ttg gat gcg gag gat cat gga tac acc atc aaa gat ttg cac agt att      864
Leu Asp Ala Glu Asp His Gly Tyr Thr Ile Lys Asp Leu His Ser Ile
        275                 280                 285 gtt tcc ttg caa gcc gtc ccg gat ggt ttc aat ccc gcg atc ctt cag      912
Val Ser Leu Gln Ala Val Pro Asp Gly Phe Asn Pro Ala Ile Leu Gln
    290                 295                 300 cgt agt cag ata gca tgg ttc ttc ttc ttt atg agg cac ttc tgc gac      960
Arg Ser Gln Ile Ala Trp Phe Phe Phe Phe Met Arg His Phe Cys Asp
305                 310                 315                 320 tct atg gtc gaa ggc ttt ccg tat gtt gac acc tgc tca agt gct gtc     1008
Ser Met Val Glu Gly Phe Pro Tyr Val Asp Thr Cys Ser Ser Ala Val
                325                 330                 335
```

```
cca gtc agc gca cat atc cat gaa gtc gct cag gcg tgg tga         1050
Pro Val Ser Ala His Ile His Glu Val Ala Gln Ala Trp
        340                 345
```

<210> SEQ ID NO 4
<211> LENGTH: 349
<212> TYPE: PRT
<213> ORGANISM: Pseudomonas putida endonuclease gene sequence

<400> SEQUENCE: 4

```
Met Ala Lys Gly His Pro Gly Leu Pro Lys Pro Asn Val Val Thr Phe
1               5                   10                  15

Ser Lys Ser Glu Leu Leu Glu Gln Leu Met Ala Val Asp Leu Asp Pro
            20                  25                  30

Ser Ala Arg Ala Arg Ala Leu Ala Met Glu Glu Gln Phe Arg Arg Lys
        35                  40                  45

Ile Asp Ser His Val Gly Ser Leu Thr Ala Ala Asp Ala Lys Phe Asn
    50                  55                  60

Lys Phe Phe Thr Ser Pro Tyr Val Leu Leu Met His Ala Arg Lys Asn
65                  70                  75                  80

Arg Tyr Thr Arg Val Ser Glu Ile Glu His Asp Ile Leu Pro Ala Lys
                85                  90                  95

Leu Phe Ser Ser Met Glu Thr Ser Ala Gly Arg Ala Val Glu Ile Ile
            100                 105                 110

Ala Leu Pro Val Tyr Gly Trp Thr Pro Val Val Ser Ala Met His Ser
        115                 120                 125

Ala Asn Ser Ala Leu Asp Gly Leu Arg Val Asn Gly Asp Thr Leu Gln
    130                 135                 140

Val Ala Thr Leu Lys Ser Gly Pro Arg Cys Leu Asn Asp Glu Met Ser
145                 150                 155                 160

Glu Asn Phe Ala Asp Thr Ile Ile Ala Asn Leu Glu Ala Trp Ala Asn
                165                 170                 175

Gln His Asp Val Arg Lys Val Glu Phe Thr Tyr Gly Val Leu Tyr Gly
            180                 185                 190

Thr Gln Lys Val Ser Asn Lys Lys Asp Trp His Ile Phe Lys Asn Leu
        195                 200                 205

Ala Leu Lys Leu Pro Glu Gly Ser Phe Ser Val Leu Pro Asn Gly Arg
    210                 215                 220

Trp Asp Cys Ser Phe Ala Tyr Lys Gly Ile Glu Val Glu Ala Gly Ile
225                 230                 235                 240

Arg Ile Gly Lys Asp Trp Thr His Leu Gly Gly Arg Leu Gly Leu
                245                 250                 255

Ala Glu Leu Ala Ile Ala Leu Ile Arg Ala Cys Ile Ala Pro Gly Asp
            260                 265                 270

Leu Asp Ala Glu Asp His Gly Tyr Thr Ile Lys Asp Leu His Ser Ile
        275                 280                 285

Val Ser Leu Gln Ala Val Pro Asp Gly Phe Asn Pro Ala Ile Leu Gln
    290                 295                 300

Arg Ser Gln Ile Ala Trp Phe Phe Phe Met Arg His Phe Cys Asp
305                 310                 315                 320

Ser Met Val Glu Gly Phe Pro Tyr Val Asp Thr Cys Ser Ser Ala Val
                325                 330                 335

Pro Val Ser Ala His Ile His Glu Val Ala Gln Ala Trp
            340                 345
```

-continued

```
<210> SEQ ID NO 5
<211> LENGTH: 46
<212> TYPE: DNA
<213> ORGANISM: Modified Promoter

<400> SEQUENCE: 5
agatcttctt gagatccttt taggtcctgc gtaatctgct gccggc           46

<210> SEQ ID NO 6
<211> LENGTH: 24
<212> TYPE: DNA
<213> ORGANISM: Reverse primer that anneals to ppuMIM start site

<400> SEQUENCE: 6
cgctgtaact cgacatgctc tgtc                                   24

<210> SEQ ID NO 7
<211> LENGTH: 21
<212> TYPE: DNA
<213> ORGANISM: ppuMIM upstream primer known from initial 5A sequencing

<400> SEQUENCE: 7
gactacggtt gcgcagtcga g                                      21

<210> SEQ ID NO 8
<211> LENGTH: 24
<212> TYPE: DNA
<213> ORGANISM: primer

<400> SEQUENCE: 8
ttcaccagtc cgtatgtctt gctg                                   24

<210> SEQ ID NO 9
<211> LENGTH: 24
<212> TYPE: DNA
<213> ORGANISM: Primer

<400> SEQUENCE: 9
ggcatcggca gcggttaggg atcc                                   24

<210> SEQ ID NO 10
<211> LENGTH: 20
<212> TYPE: DNA
<213> ORGANISM: Primer

<400> SEQUENCE: 10
tcagcgtagt cagatagcat                                        20

<210> SEQ ID NO 11
<211> LENGTH: 36
<212> TYPE: DNA
<213> ORGANISM: Primer

<400> SEQUENCE: 11
caccaccacc atatggctgt tgatctcgac ccgagt                      36

<210> SEQ ID NO 12
<211> LENGTH: 27
<212> TYPE: DNA
<213> ORGANISM: Primer

<400> SEQUENCE: 12
caccaagaat tctaggggag tcgaacc                                27
```

```
<210> SEQ ID NO 13
<211> LENGTH: 37
<212> TYPE: DNA
<213> ORGANISM: Primer

<400> SEQUENCE: 13
caccaccacc atatggcaaa agggcatcca ggactac                              37
```